US00PP13449P2

(12) United States Plant Patent
Carruth

(10) Patent No.: US PP13,449 P2
(45) Date of Patent: Jan. 7, 2003

(54) SHRUB ROSE PLANT NAMED 'WEKSTEPHITSU'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/981,228

(22) Filed: Oct. 15, 2001

(51) Int. Cl.[7] ..... A01H 5/00
(52) U.S. Cl. ..... Plt./102
(58) Field of Search ..... Plt./101, 102, 107, Plt./108

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Shurb rose suitable for garden decoration, having flowers of Magenta to Lavender-Blue coloration.

1 Drawing Sheet

BOTANICAL CLASSIFICATION

*Rosa hybrida.*

VARIETY DENOMINATION

'WEKSTEPHITSU'.

BACKGROUND OF THE INVENTION

This invention relates to a new and distinct variety of Shrub Rose. The varietal denomination of the new variety is 'WEKSTEPHITSU'. It has as its seed parent the variety know as 'STEbigpu' (U.S. Plant Pat. No. 6,262) and as its pollen parent an undisseminated seedling of my creation.

SUMMARY OF THE INVENTION

Among the features which distinguish the new variety from other presently available and commercial rose cultivars known to the inventor are the following combination of characteristics: its moderately smooth stems with very few prickles, its unusual Magenta to Lavender-Blue coloration, its cuppy old fashion flower form and its strong fragrance. The plant has an upright to somewhat spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagation. 'WEKSTEPHITSU' may be asexually propagated by cuttings, budding and grafting.

COMPARISION WITH PARENTS

The new rose may be distinguished from its seed parent, 'STEbigpu' by the following combination of characteristics: whereas 'WEKSTEPHITSU' bears medium size flowers with a yellow coloration at the point where the petal attaches, the seed parent bears significantly larger flowers with no visible change in coloration at the point where the petal attaches. The new variety is classified as a shrub with medium size foliage whereas 'STEbigpu' is classified as a hybrid tea with significantly larger foliage.

The new variety may be distinguished from its pollen parent, an un-disseminated seedling of my creation, by the following combination of characteristics: whereas 'WEKSTEPHITSU' bears medium sized fully double (about 41 to 53 petals) flowers of Magenta to Lavender-Blue coloration, the pollen parent bears significantly smaller flowers of semi-double (about 8 to 12 petals) petalage with a blended Pink-Lavender coloration.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color refrences and/or values are based upon the The Royal Horticultural Society Colour Chart (1996) and terminology used in the color descriptions herein refers to plate numbers in this color chart except where common terms of color definition are employed.

DESCRIPTION OF THE NEW VARIETY

The following description is of 3 to 4 year-old rose plants of the new variety grown outdoors in Upland, Calif. in the month of September. Phenotypic expression may vary with light intensity, cultural and environmental conditions, as well as differences in conditions of light and soil.

FLOWER

The new variety sometimes bears its flowers singly, usually in clusters of 2 to 3 per stem. Flowers are borne in irregular flat to somewhat rounded clusters on strong medium length stems (about 30 to 52 cm). Outdoors, the plant blooms abundantly and nearly continuously during the growing season. The flowers have a strong furity to somewhat spicy fragrance.

BUD

The peduncle is about 2.6 to 4.4 cm in length, of average caliper (about 0.2 to 0.4 cm in diameter), and usually erect. It is almost smooth, with few stipitate glands and hairs. Peduncle color is between 144A and 148D sometimes lightly suffused, especially on the side exposed to the sun, with between 183B and 187C.

Before the calyx breaks, the bud is pointed to ovoid in shape and about 0.9 to 1.5 cm in diameter at the widest point, about 1.2 to 1.8 cm in length. The surface of the bud bears few foliaceous appendages and numerous stipitate glands, usually with slender entire foliaceous parts extending beyond the tip of the bud about ½ of its length. Bud color is between 144A and 148D sometimes lightly suffused, especially on the side exposed to the sun, with between 183B and 187C.

The sepals are about 1.9 to 2.8 cm in length and about 0.6 to 1.0 cm in width at the widest point. The outer surface of the sepal is between 144A and 148D sometimes lightly suffused with between 183B and 187C. The inner surface of the sepal is between 143A and 139D and covered with fine wooly tomentum; sepal margins are lined with some stipitate glands and hairs.

As the petals open (after the calyx breaks), the bud is pointed to somewhat ovoid in form, about 1.4 to 2.0 cm in diameter at the widest point, about 1.9 to 2.7 cm in length.

The color of the under surface of newly opened petals is between 59B and 60B. At the point where the petal attaches, there is a large zone of between 5C and 6C. The upper surface color of the newly opened petals is between 60A and 53A. At the point where the petal attaches, there is a moderately large zone of between 12A and 14B.

BLOOM

When fully open, the bloom ranges from about 6.2 to 8.3 cm in diameter. Petalage is double with about 41 to 53 petals and 1 to 5 petaloids irregularly arranged.

When partially open, the bloom form is cupped, and the petals are somewhat cupped with the petal edges very slightly reflexed outward. When fully open, the bloom form is more loosely cupped, and the petals are more cupped to slightly undulated with petal edges slightly reflexed outward.

PETALS

The substance of the petals is moderately light and somewhat thin, with upper surface moderately satiny and under surface matte to slightly shiny.

The outer petals are broadly obovate in shape with rounded apices and sometimes slightly notched with one notch. The inner petals are obovate in shape with rounded apices.

The petals are about 3.5 to 3.9 cm in length and about 2.7 to 3.2 cm in width at the widest point. Petal margins are entire.

NEWLY OPENED FLOWER

At the point where petals attach, on the under surface of the outer intermediate and inner petals, there is a large zone of between 9C and 14D that gradually suffuses toward the petal edge to as dark as between 61B and 60B. The upper surface of the outer, intermediate and inner petals is between 61B and 60B. At the point where the petal attaches, there is a moderately large zone of between 9B and 14C.

The general tonality of the newly opened flower is between 61B and 60B.

THREE-DAY-OLD FLOWER

At the point where the petal attaches, on the under surface of the outer and inner petals, there is a very large zone of between 4C and 8D that gradually suffuses toward the petal edge to as dark as between 78C and 72B. The upper surface of the outer petals is between 70B and 72B. At the point where the petal attaches, there is a moderately large zone of between 5C and 8C.

The general tonality of the three-day-old flower is between 70B and 72B.

On the spent bloom, the petals usually drop off cleanly.

In September in Upland, Calif., blooms on the bush growing outdoors generally last about 4 to 5 or more days. Cut roses from plants grown outdoors and kept at normal indoor living temperatures generally last about 4 to 5 or more days.

MALE REPRODUCTIVE ORGANS

Stamens are many in number (average about 85) and are arranged regularly about the pistils; a few are mixed with petaloids. The filaments are of somewhat short length (about 0.4 to 0.6 cm), most with anthers. Filaments are between 13A and 14B in color. The anthers are somewhat small for the class and all open approximately at the same time. Anther color is between 16B and 21C when immature and between 200B and 164C at maturity. Pollen is abundant.

FEMALE REPRODUCTIVE ORGANS

Pistils vary in number (average about 45). The styles are moderately even, average in length (about 0.4 to 0.6 cm), somewhat thin in caliper, and moderately loosely bunched. Stigma color is between 4B and 5C. Style color is between 1D and 2D sometimes very lightly suffused with near 53D. Ovaries are usually all enclosed in the calyx.

Hips are short in length (about 1.0 to 1.5 cm), moderately globular in form, and between 23A and 21A in color when ripe. The hip surface is very smooth with thick fleshy walls. The sepals are somewhat permanent, medium in length, and usually straight in shape. The seeds are irregularly rounded, smooth in texture, approximately 4 to 8 per hip, about 0.4 to 0.7 cm. in diameter at the widest point and between 160B and 162C in color.

FOLIAGE

The compound leaves are ususally comprised of 3 to 5 or more leaflets and are borne abundantly. The five-leaflet leaves are about 10.5 to 12.7 cm in length and about 7.6 to 8.4 cm in width at the widest point, moderately heavy to somewhat leathery in texture, and semi-glossy in finish. The terminal leaflets are about 4.1 to 5.8 cm in length and about 2.5 to 4.1 cm in width at the widest point, shaped ovate to broadly oval with moderately acute to somewhat acuminate apices and moderately rounded to slightly acute bases. Their margins are usually simply serrate.

The upper surface of the mature leaf is between 137B and 147A. The under surface of the mature leaf is between 146B and 148C. The upper surface of the young leaf is between 137C and 146A, sometimes moderately suffused with between 183B and 187B. The under surface of the young leaf is between 138B and 146C, sometimes moderately suffused with between 183B and 187B.

The rachis is average in caliper and somewhat rough. The upper side is shallowly grooved with some hairs and stipitate glands on the edges of the grooves. The under side of the rachis is somewhat rough, usually with some stipitate glands and few small prickles. The rachis color is between 145B and 144B.

The stipules are about 1.2 to 1.7 cm in length and moderately wide (about 0.5 to 0.8 cm) with very long straight points that usually turn out at an angle of more than 45 degrees. The color of the stipules is between 137C and 146B.

The petiole is about 0.7 to 1.2 cm in length and about 0.2 to 0.3 cm in diameter at the widest point. The color of the petiole is between 137C and 146B.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright to somewhat spreading growing habit (about 125 to 140 cm in height and about 105 to 125 cm spread at the widest point), with very full branching. It displays moderately vigorous growth and the canes are of somewhat light to medium caliper for the class.

The color of the major stems is between 146B and 146C. They bear very few large prickles that are about 0.6 to 0.9 cm in length. The large prickles are almost straight angled slightly downward with a moderately long broad oval base; prickle color is between 164A and 165B. The major stem bears very few small prickles of similar shape and coloration.

The color of the branches is between 144A and 148B. They bear very few large prickles which are of similar size and shape to the large prickles on the major stems; prickle color is between 160A and 161B. The branches bear very few small prickles of similar shape and coloration.

The color of the new shoots is between 144B and 148B sometimes lightly suffused with between 183B and 187B. They bear few large prickles which are of similar size and shape to the large prickles on the major stems; prickle color is between 160A and 160B often heavily suffused with between 183D and 184A. The shoots bear few small prickles of similar shape and coloration.

I claim:

1. A new and distinct Shrub rose plant of the variety substantially as described and illustrated herein.

* * * * *

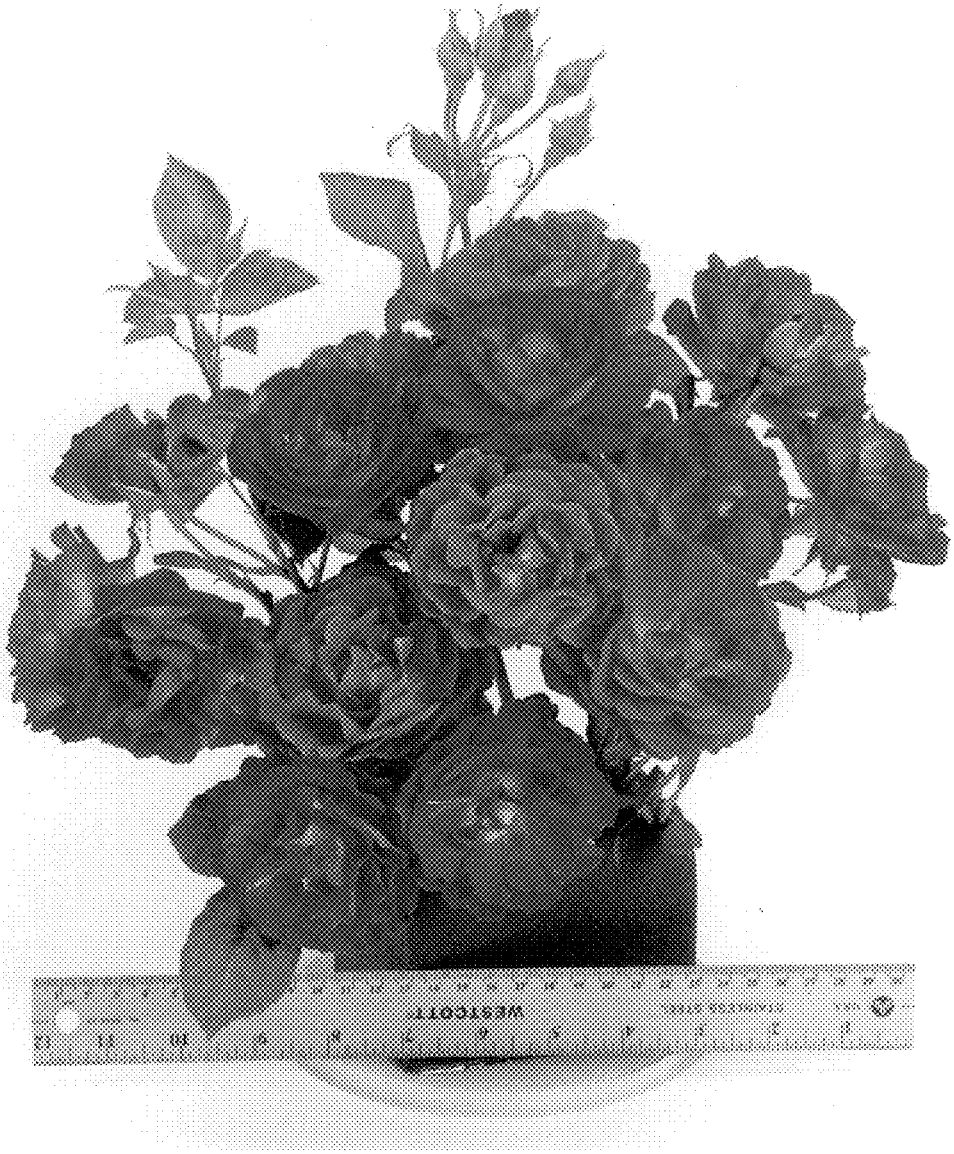
WESTCOTT